United States Patent
Lee et al.

(10) Patent No.: US 9,151,752 B2
(45) Date of Patent: Oct. 6, 2015

(54) METHOD FOR AMPLIFYING VARIATION OF FREQUENCY OF SIGNAL IN PIEZOELECTRICAL BIOSENSOR

(71) Applicant: Samsung Electronics Co., Ltd., Suwon-Si (KR)

(72) Inventors: Hun Joo Lee, Seoul (KR); Soo Suk Lee, Suwon-si (KR)

(73) Assignee: SAMSUNG ELECTRONICS CO., LTD. (KR)

(*) Notice: Subject to any disclaimer, the term of this patent is extended or adjusted under 35 U.S.C. 154(b) by 384 days.

(21) Appl. No.: 13/859,984

(22) Filed: Apr. 10, 2013

(65) Prior Publication Data
US 2013/0224732 A1    Aug. 29, 2013

Related U.S. Application Data

(62) Division of application No. 12/099,896, filed on Apr. 9, 2008, now Pat. No. 8,440,468.

(30) Foreign Application Priority Data

Dec. 27, 2007    (KR) .................. 10-2007-0139039

(51) Int. Cl.
*G01N 33/553* (2006.01)
*G01N 33/543* (2006.01)

(52) U.S. Cl.
CPC .... *G01N 33/54393* (2013.01); *G01N 33/54373* (2013.01)

(58) Field of Classification Search
None
See application file for complete search history.

(56) References Cited

U.S. PATENT DOCUMENTS

| | | |
|---|---|---|
| 5,501,986 A | 3/1996 | Ward et al. |
| 6,180,415 B1 | 1/2001 | Schultz et al. |
| 7,052,854 B2 | 5/2006 | Melker et al. |
| 2010/0105079 A1 | 4/2010 | Warthoe |

OTHER PUBLICATIONS

Gadi Peleg et al., "Nonliner optical measurement of membrane potential around single molecules at selected cellular sites," Proc. Natl. Acad. Sci. USA, vol. 96, Hune 1999, pp. 6700-6704.
Seydack M., "Nanoparticle labels in immunosensing using optical detection methods," Biosens Bioelectron, vol. 20, No. 12, Jun. 15, 2005, pp. 2454-2469.
Xia Chu et al., "Silver-enhanced colloidal gold metalloimmunoassay for *Schistosoma japonicum* antibody detection," Journal of Immunological Methods, vol. 301, 2005, pp. 77-88.
Xiaodi Su et al., "Au nanoparticle- and silver-enhancement reaction-amplified microgravimetric biosensor,"Chem. Commun., 2001, pp. 755-756.

*Primary Examiner* — Chris L Chin
(74) *Attorney, Agent, or Firm* — Cantor Colburn LLP (57) ABSTRACT

Provided is a method for amplifying a frequency variation of a detected signal in a biosensor that is used for detecting a biomolecule by measuring a change in frequency of an oscillating signal, the change being caused by pressure a biomolecule applies to a piezoelectric substance. The method for amplifying a frequency variation of a detected signal comprises the steps of: (a) applying a sample to a probe being fixed to an upper portion of a substrate of the biosensor to allow a biomolecule in the sample to be bound to the probe; (b) applying protein tagged with a metal particle to the biosensor to allow the protein and the biomolecule to be bound with each other; and (c) applying a metal enhancer to the biosensor to allow the metal enhancer to be bound to the metal particle having been bound to the protein.

16 Claims, 7 Drawing Sheets

METHOD FOR AMPLIFYING VARIATION OF FREQUENCY OF SIGNAL IN PIEZOELECTRICAL BIOSENSOR

CROSS-REFERENCE(S) TO RELATED APPLICATIONS

The present invention is a divisional of U.S. patent application Ser. No. 12/099,896, filed on Apr. 9, 2008, which claims priority of Korean patent application number 10-2007-0139039, filed on Dec. 27, 2007, which is incorporated by reference in its entirety.

BACKGROUND OF THE INVENTION

1. Field of the Invention

The present invention relates to a method for amplifying the frequency of a detected signal in a piezoelectric biosensor.

2. Description of the Related Art

Biosensors using a piezoelectric substance, for example, SAW (surface acoustic wave) filter sensors, QCMs (quartz crystal microbalances), cantilevers, FBAR (film bulk acoustic resonance) filters, and the like, can analyze a specific bio substance in a sample quantitatively and qualitatively.

To this end, biomolecules such as proteins, DNA, virus, bacteria, animal cells, plant cells, tissues, etc., and biomolecule products such as a toxin, etc., produced from such biomolecules (both biomolecules and biomolecule products will be referred to collectively as "biomolecules" in the specification) are specifically bound to the surface of the biosensor.

The specifically bound biomolecule changes mass on the surface of a biosensor, and this varies the oscillation frequency of a detected signal in the biosensor. Therefore, quantitative or qualitative analysis on a target biomolecule in a sample can be achieved by monitoring the oscillation frequency. Further, the analysis result on the biomolecule in a sample is then usefully applied to diagnosis or monitoring of a disease of interest.

SUMMARY OF THE INVENTION

The present invention is to provide a method for amplifying the frequency of a detected signal in a piezoelectric biosensor.

Further, the present invention is to provide a biomolecule detection kit used for amplifying the frequency of a detected signal in a biosensor.

Further, the present invention is to provide a method of operation the biomolecule detection kit.

In accordance with an aspect of the present invention, there is provided a method for amplifying frequency variation of a detected signal in a biomolecule detecting biosensor, the method comprising the steps of: (a) applying a sample to a probe being fixed to an upper portion of a substrate of the biosensor so as to allow a biomolecule in the sample to be bound to the probe; (b) applying protein tagged with a metal particle to the biosensor to allow the protein and the biomolecule to be bound with each other; and (c) applying a metal enhancer to the biosensor so as to allow the metal enhancer to be bound to the metal particle which is bound to the protein.

In accordance with another aspect of the present invention, there is provided a method for amplifying frequency variation of a detected signal in a biomolecule detecting biosensor, the method comprising the steps of: (a) applying a metal particle to a sample so as to allow a biomolecule in the sample to be tagged with the metal particle; (b) applying the sample containing the biomolecule tagged with the metal particle to a probe which is fixed to an upper portion of a substrate of the biosensor such that the biomolecule in the sample and the probe are bound with each other; and (c) applying a metal enhancer to the biosensor so as to allow the metal enhancer to be bound to the metal particles which is bound to the biomolecule.

Further, in accordance with another aspect of the present invention, there is provided a biomolecule detection kit comprising: a biosensor, in which a probe capable of being bound to a biomolecule specifically is fixed to a surface of a substrate and which outputs an oscillating signal depending on a pressure the biomolecule applies to a piezoelectric substance; and protein which is tagged with a metal particle and which can be bound to the biomolecule specifically.

Further, in accordance with an aspect of the present invention, there is provided an operation method of a biomolecule detection kit, the method comprising the steps of: applying a sample to a probe being fixed to an upper portion of a surface of a substrate of a biosensor so as to allow a biomolecule in the sample to be bound to the probe; (b) applying protein tagged with a metal particle to the biosensor so as to allow the protein and the biomolecule to be bound with each other; and (c) applying a metal enhancer to the biosensor to allow the metal enhancer to be bound to the metal particle which is bound to the protein.

The other objectives and advantages of the invention will be understood by the following description and will also be appreciated by the embodiments of the invention more clearly. Further, the objectives and advantages of the invention will readily be seen that they can be realized by the means and its combination specified in the claims.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF EXEMPLARY EMBODIMENTS

Hereinafter, exemplary embodiments of the present invention will be described in detail with reference to the accompanying drawings so that those skilled in the art can easily carry out the invention.

Figure 1:
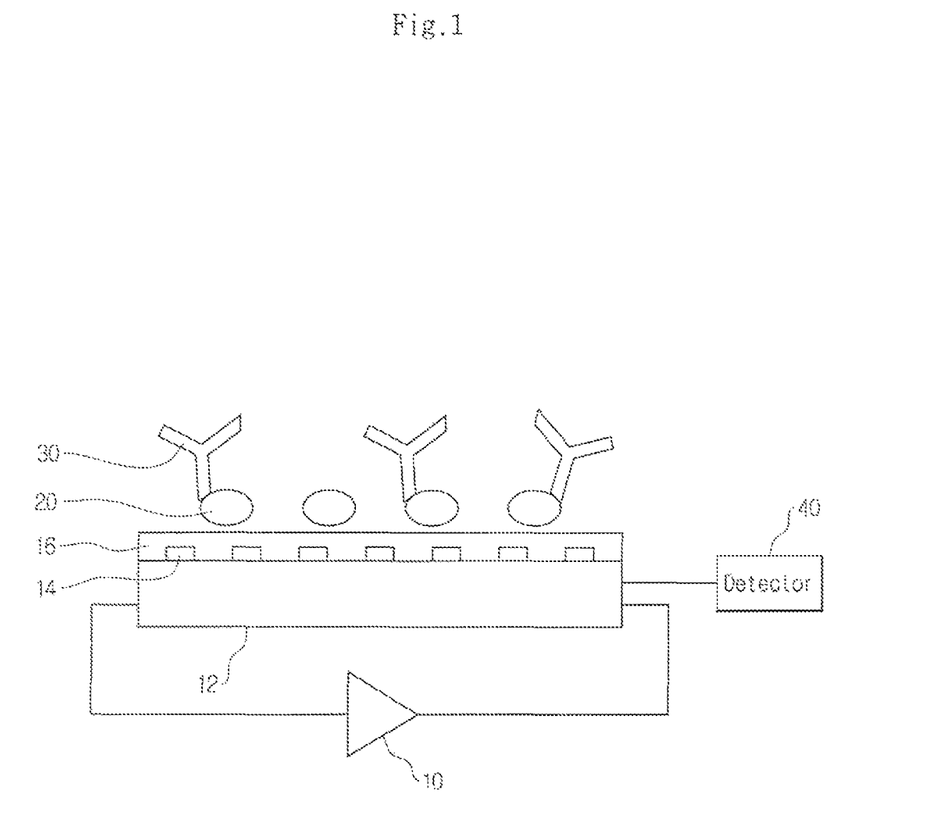
FIG. 1 is a schematic view of a SAW sensor in a biosensor to which the present invention is applied.

FIG. 1 is a schematic view of a Love-type SAW sensor using a horizontal wave, shown as an example of a biosensor that can adopt a method for amplifying a frequency variation of a detected signal according to one embodiment of the present invention. The SAW sensor includes an oscillator 10, a substrate 12, an IDT (inter digital transducer) 14, a guide layer 16, and a probe 20.

When an electric oscillating signal from the oscillator 10 is applied to the IDT electrode 14 in the SAW sensor, the electric oscillating signal is converted into a mechanical waveform by the IDT electrode 14. Then the mechanical waveform is conveyed via the guide layer 16 made of a polymer compound or $SiO_2$. At this time, the mechanical waveform experiences a frequency change caused by a biomolecule 30 that specifically bound to the probe 20 fixed to an upper portion of the guide layer 16. The mechanical waveform is converted into an electrical signal by a detector 40. That is to say, the detector 40 detects a change in frequency of the mechanical waveform, and converts it into an electrical signal, in which the change is induced by the biomolecule 30.

As such, the biomolecule can be analyzed quantitatively or qualitatively based on the monitoring result on a frequency change in a detected signal being caused by the biomolecule.

While this embodiment used a SAW sensor as a biosensor, a QCM, cantilever, or FBAR may also be used if necessary.

Figure 2:
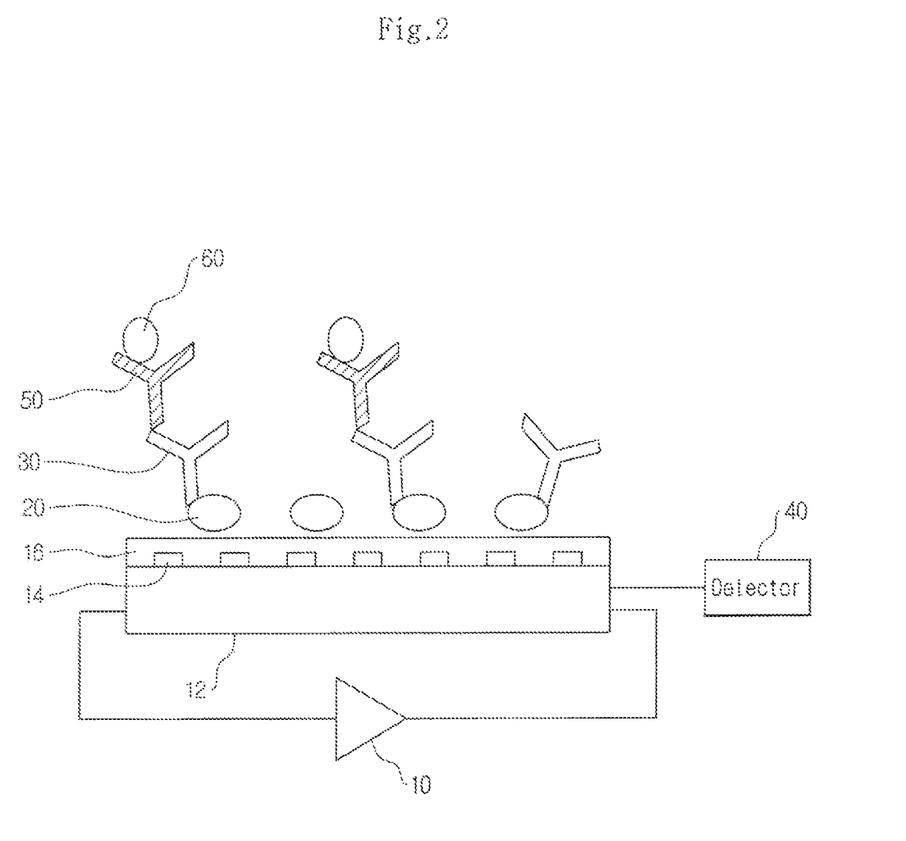
FIGS. 2 and 3 respectively illustrate a method for amplifying a frequency variation of a signal detected and output by a biosensor in accordance with a first embodiment of the present invention.
Figure 3:
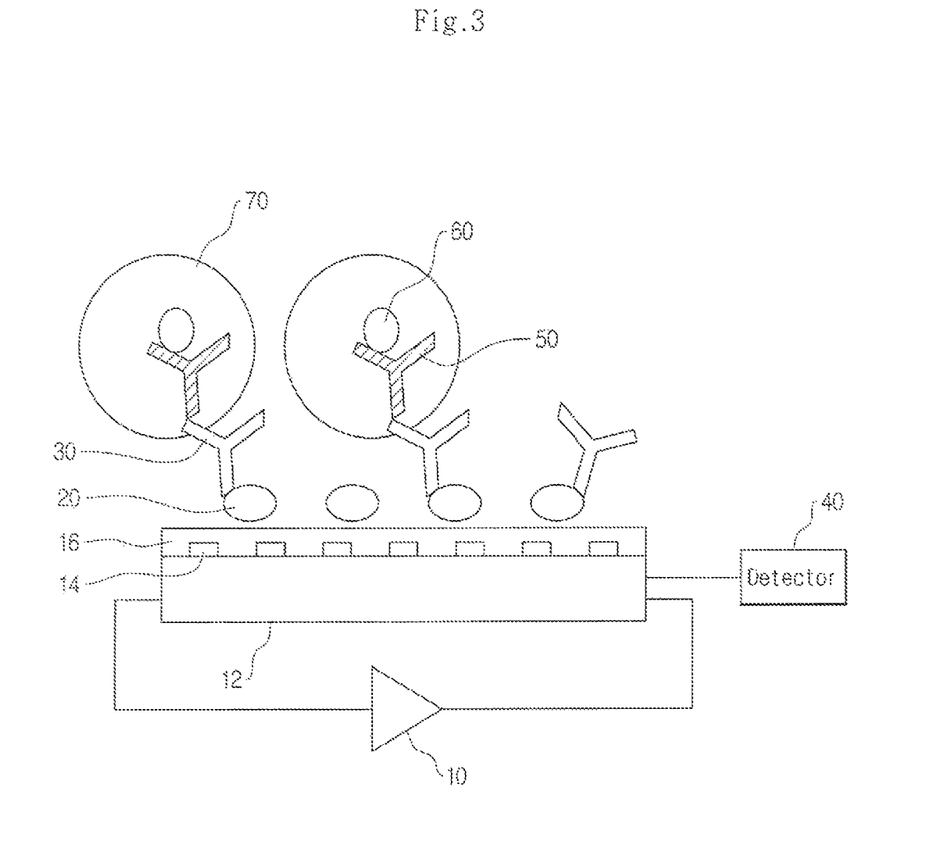
Figure 4:
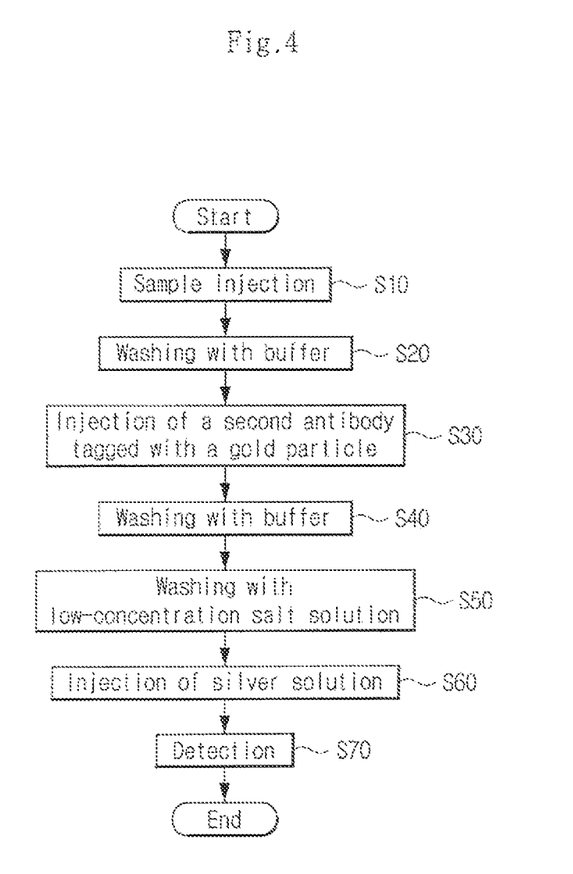
FIG. 4 is a flow chart describing a method for amplifying a frequency variation of a signal detected and output by a biosensor in accordance with the first embodiment of the present invention.

FIGS. 2 and 3 respectively illustrate a method for amplifying a frequency variation of a signal detected and output by a biosensor in accordance with a first embodiment of the present invention, and FIG. 4 is a flow chart describing the method of the first embodiment.

The method according to the first embodiment of the present invention will now be explained, with referring to FIGS. 2 through 4.

At first, a probe 20 is chemically fixed to an upper portion of a substrate 12 (i.e. an upper portion of a guide layer 16) of the SAW sensor. Next, a sample (for example, urine or blood of a patient) is applied to the fixed probe 20 so that a biomolecule 30 contained in the sample binds to the probe 20 (S10). Here, a specific biomolecule 30 in the sample is biologically specifically bound to the probe 20.

Then, a surface of the SAW sensor is washed with buffer solution (S20) to prevent any nonspecific binding.

Then, a second antibody (a kind of protein) 50 tagged with metal particles (e.g., gold particles) 60 is applied to the surface of the SAW sensor so as to cause the second antibody 50 to be bound to the biomolecule 30 (S30). The gold particles 60 have preferably a diameter of several hundred nanometers or less, and more preferably 100 nanometers or less. The second antibody 50 is protein that specifically binds to the biomolecule 30. FIG. 2 shows that second antibody 50 tagged with the gold particle 60 is bound to the biomolecule 30 in the sample.

Next, the surface of the SAW sensor is washed again with buffer solution (S40) and then with low-concentration salt solution (S50) subsequently. The reason for using low-concentration salt solution, not high-concentration salt solution, is to prevent salt from binding to a metal enhancer, which will be added later, and from producing any precipitate (e.g., AgCl). Therefore, the surface of the SAW sensor should be washed with salt-free solution or low-concentration salt solution or salt solution without salts that can produce precipitates. To increase the efficiency of the amplification, the buffer solution used for washing the SAW sensor should not contain $Cl^-$, $Br^-$, $I^-$ nor $F^-$, each of which is able to bind with Ag to produce precipitates and inhibiting $Ag^-$ from binding to gold particles, or should contain the least amount thereof.

Then, a solution containing a metal enhancer (e.g., silver ion) 70 is applied to the surface of the SAW sensor so that the metal particle 60 having been bound to the second antibody 50 may be bound with the silver ion 70 (S60). As shown in FIG. 3, the silver ion 70 is bound to the gold particle 60 having been bound to the second antibody 50.

As shown, the biomolecule 30 in the sample is specifically bound to the probe 20 fixed onto the surface of the SAW sensor, and the metal enhancer 70 is bound additionally to the biomolecule 30 by the medium of the second antibody 50 and the metal particle 60, so that more pressure can be applied to the SAW sensor. Therefore, a frequency variation of a signal generated by the biomolecule 30 bound to the probe 20 can be increased, and it becomes easier for the detector 40 to detect an output signal of the SAW sensor and monitor frequency changes (S70). Even though there is a very small amount of the biomolecule 30 to be detected in the sample, a variation in frequency of a detected signal can be increased. Therefore, LOD (Limit of Detection) of the sensor is enhanced.

However, if there is no biomolecule 30 to be detected in the sample, it means that there is no substance being specifically bound to the probe 20. Therefore, a signal would not be amplified nor changed even if the metal enhancer is applied to the surface of the SAW sensor.

Meanwhile, using a SAW sensor whose surface is blocked with a substance that does not bind to the biomolecule as a reference SAW sensor, the biomolecule in the sample may be analyzed quantitatively and qualitatively based on comparison results on detected signals that are produced under the same experimental conditions.

Figure 5:
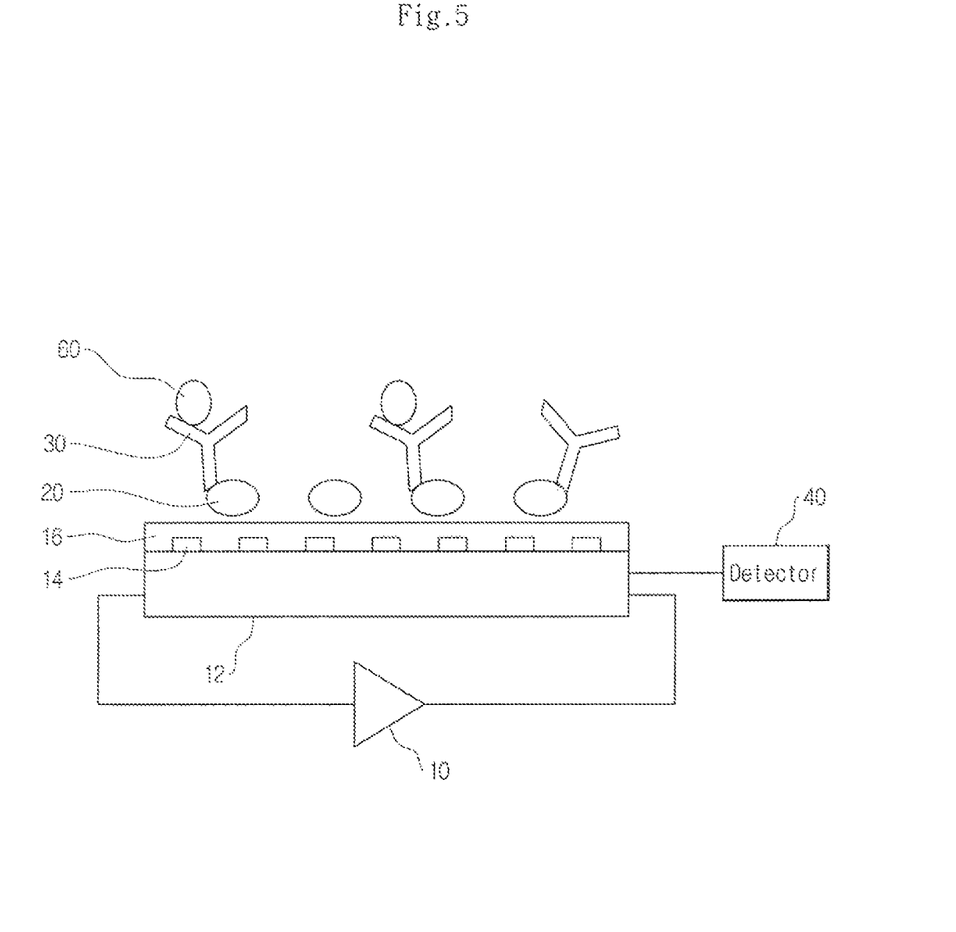
FIGS. 5 and 6 respectively illustrate a method for amplifying a frequency variation of a signal detected and output by a biosensor in accordance with a second embodiment of the present invention.
Figure 6:
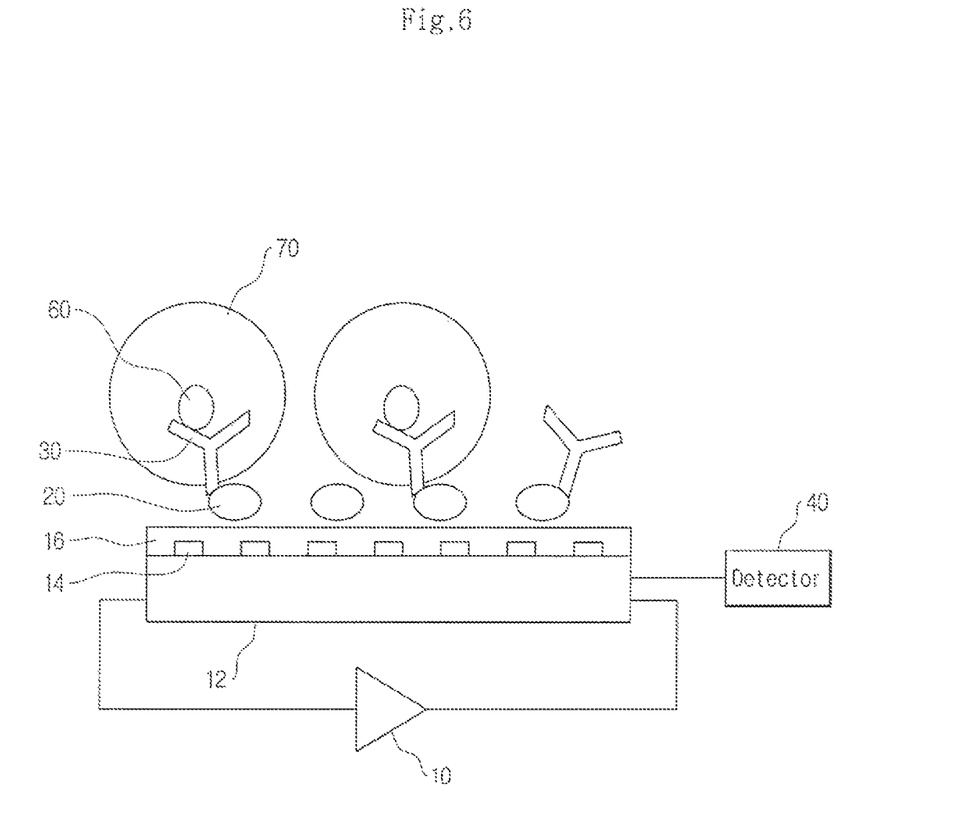
Figure 7:
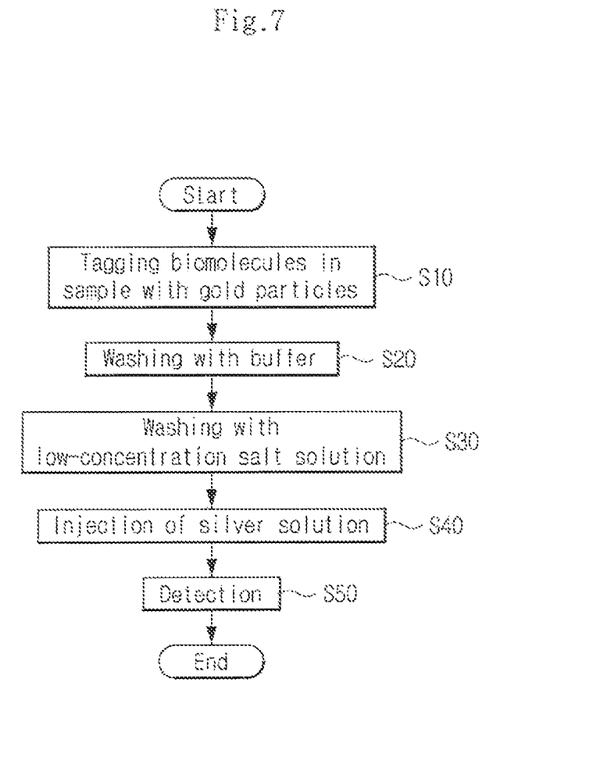
FIG. 7 is a flow chart describing a method for amplifying a frequency variation of a signal detected and output by a biosensor in accordance with the second embodiment of the present invention.

FIGS. 5 and 6 respectively illustrate a method for amplifying a frequency variation of a signal detected and output by a biosensor according to a second embodiment of the present invention, and FIG. 7 is a flow chart describing the method of the second embodiment. The second embodiment differs from the first embodiment in that metal particles were bound directly to biomolecules in a sample, without using a second antibody.

The method of the second embodiment will now be explained in detail, referring to the FIGS. 5 through 7.

To begin with, metal particles (e.g., gold particles) 60 are applied to a sample so that a biomolecule 30 in the sample binds to the metal particles 60. The sample containing the biomolecule 30 tagged with metal particles 60 is then applied to the surface of the SAW sensor to allow the biomolecule 30 in the sample to be bound to a probe 20 fixed on an upper portion of the substrate (S10). As shown in FIG. 5, biomolecule 30 tagged with the gold particle 60 in the sample is bound to the probe.

Next, the surface of the SAW sensor is washed with buffer solution (S20) and then with low-concentration salt solution (S30) subsequently.

Then, a solution containing a metal enhancer (e.g., silver ion) 70 is applied to the surface of the SAW sensor so that the metal particle 60 having been bound to the biomolecule 30 may be bound with the silver ion 70 (S40). As shown in FIG. 6, the silver ion 70 is bound to the gold particle 60 having been bound to the biomolecule 30.

Therefore, similar to the first embodiment, the biomolecule 30 in the sample is specifically bound to the probe 20 fixed onto the surface of the SAW sensor, and the metal enhancer 70 is bound additionally to the biomolecule 30 by the medium of the metal particle 60. More pressure can be applied to the SAW sensor and a frequency variation of a signal generated by the biomolecule 30 bound to the probe 20 can be increased. It becomes easier for the detector 40 to detect an output signal of the SAW sensor and monitor frequency changes (S70).

The present invention further provides a biomolecule detection kit to easily amplify the frequency variation of a detected signal in the biosensor when a biosensor is used to detect a biomolecule. The biomolecule detection kit according to an embodiment of the present invention includes a biosensor in which a probe capable of being bound to a specific biomolecule is fixed to the surface of a substrate and which outputs an oscillating signal depending on a pressure the biomolecule applies to a piezoelectric substance; and protein which is bound to a metal particle and which is capable of being bound to a specific biomolecule.

For operation of the biomolecule detection kit, a sample is applied to the probe being fixed to the substrate surface of the biosensor so as to allow a biomolecule in the sample to be bound to the probe. Then protein tagged with metal particles is applied to the biosensor so that the protein and the biomolecule are bound with each other. Finally, a metal enhancer is applied to the biosensor so that the metal enhancer is bound to the metal particles having been bound to the protein.

Therefore, the biomolecule is specifically bound to the probe being fixed onto the surface of the biosensor, and the metal enhancer is bound additionally to the biomolecule. In result, more pressure can be applied to the biosensor and a frequency variation of a signal generated by the biomolecule bound to the probe can be increased. It becomes easier for a detector to detect an output signal of the biosensor and monitor frequency changes.

While the present invention has been described with respect to the specific embodiments, it will be apparent to those skilled in the art that various changes and modifications may be made without departing from the spirit and scope of the invention as disclosed in the following claims.

What is claimed is:

1. A method for amplifying frequency variation of a detected signal in a biomolecule detecting biosensor, the method comprising the steps of:
   (a) applying a metal particle to a sample to allow a biomolecule in the sample to be tagged with the metal particle:
   (b) applying the sample containing the biomolecule tagged with the metal particle to a probe which is fixed to an upper portion of a substrate of the biosensor to allow the biomolecule in the sample to be bound to the probe; and
   (c) washing the surface of the biosensor with buffer solution which does not contain salt capable of producing a precipitate or which contains low-concentration salt; and
   (d) applying a metal enhancer to the biosensor to allow the metal enhancer to be bound to the metal particles which is bound to the biomolecule.

2. The method of claim 1, wherein the biosensor is SAW sensor, QCM, cantilever, or FBAR filter.

3. The method of claim 1, wherein the probe is chemically bound to the upper portion of the substrate of the biosensor.

4. The method of claim 1, wherein, in step (b), the probe and the biomolecule are bound with each other biologically specifically.

5. The method of claim 1, wherein the metal particle is a gold particle.

6. The method of claim 1, wherein the metal enhancer is a silver ion.

7. A method for detecting a biomolecule in a sample by detecting a change of an electric signal, comprising:
   applying a metal particle to the sample to allow a biomolecule in the sample to be tagged with the metal particle;
   applying the sample containing the biomolecule tagged with the metal particle to a probe with is fixed to a substrate of a biosensor to allow the biomolecule in the sample to be bound to the probe;
   washing the surface of the biosensor with buffer solution which does not contain salt capable of producing a precipitate or which contains low-concentration salt;
   applying a metal enhancer to the biosensor to allow the metal enhancer to be bound to the metal particle which is bound to the biomolecule;
   detecting the change between the electric signal prior to the biomolecule bonding to the probe, and the electric signal after the biomolecule bonds to the probe and the metal enhancer bonds to the metal particle; and
   detecting quantitatively or qualitatively the biomolecule based on the change in the electric signal.

8. The method of claim 7, wherein the biosensor is SAW (surface acoustic wave) sensor, QCM (quartz crystal microbalance), cantilever, or FBAR (film bulk acoustic resonance) filter.

9. The method of claim 7, wherein the probe is chemically bound to the upper portion of the substrate of the biosensor.

10. The method of claim 7, wherein, the probe and the biomolecule are bound with each other biologically specifically.

11. The method of claim 7, wherein the metal particle is a gold particle.

12. The method of claim 7, wherein the metal enhancer is a silver ion.

13. The method of claim 7, wherein the washing comprises washing the piezoelectric biosensor with a buffer solution which does not contain salt capable of producing a precipitate and then with a low-concentration salt solution subsequently.

14. The method of claim 7, wherein the biomolecule in the sample is selected from the group consisting of proteins, DNAs, virus, bacteria, animal cells, plant cells, tissues and products produced from any one of the biomolecule.

15. The method of claim 7, wherein the detecting the change of the electric signal comprises detecting an amplified frequency variation of the electric signal.

16. The method of claim 7, wherein the metal enhancer is applied in a form of a solution containing a metal enhancer.

* * * * *